United States Patent [19]

Nikl et al.

[11] Patent Number: 5,147,862

[45] Date of Patent: Sep. 15, 1992

[54] COMPOSITION AND PROCESS TO ENHANCE THE EFFICACY OF A FISH VACCINE

[75] Inventors: Libor Nikl; Lawrence Albright, both of Burnaby, Canada

[73] Assignee: Taito Co., Ltd., Tokyo, Japan

[21] Appl. No.: 313,033

[22] Filed: Feb. 21, 1989

[51] Int. Cl.⁵ .......................................... A61K 31/715
[52] U.S. Cl. .................. 514/54; 424/195.1; 514/885
[58] Field of Search ............... 514/54, 885; 424/195.1

[56] References Cited

U.S. PATENT DOCUMENTS 3,943,247  3/1976  Komatsu et al. ..................... 514/54

FOREIGN PATENT DOCUMENTS 2570081   3/1986   France .
56-99423  8/1981   Japan .
56-156216 12/1981  Japan .

OTHER PUBLICATIONS

Chem. Abst. 113:184712q, 1990.
Chem. Abst. 97:120247k, 1982.
Chem. Abst. 97:12048w, 1982.

*Primary Examiner*—John W. Rollins
*Attorney, Agent, or Firm*—Townsend and Townsend

[57] ABSTRACT

A process and composition to enhance the efficacy of a fish vaccine. A β-1,3-glucan having a β-1,3-linked main chain with β-1,6-linked single glucose side chains is administered to a fish treated with the vaccine.

9 Claims, 1 Drawing Sheet

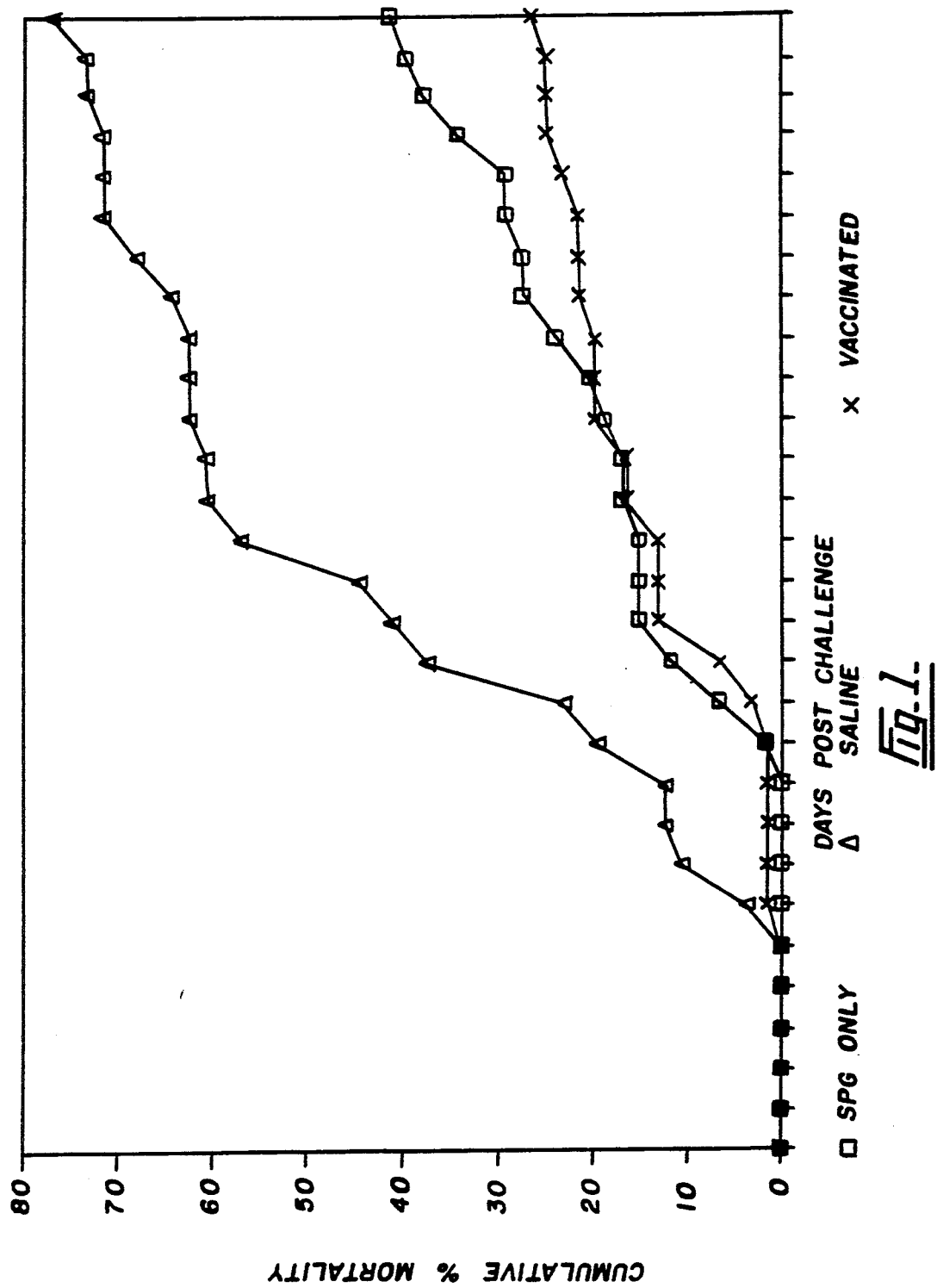

COMPOSITION AND PROCESS TO ENHANCE THE EFFICACY OF A FISH VACCINE

FIELD OF THE INVENTION

This invention relates to a process to enhance the efficacy of a fish vaccine and to a process to stimulate the immune system of a fish and to a composition useful in these processes.

DESCRIPTION OF THE PRIOR ART

Fish rearing in fish farms is increasingly evident. The advantages of aquaculture in comparison to fishing wild stocks is as apparent as the keeping of cattle compared with the hunting of wild animals. However, there are problems. The fish must be kept at a very high density and this means that the fish are susceptible to disease and, in particular, to the rapid spread of disease through the fish farm. Aquaculture techniques are improving all the time and the use of antibiotics, usually administered in the food, has been a major advantage in reducing disease. Nevertheless the use of antibiotics in this way can lead to the development of resistant strains of fish pathogens. There is also a popular sentiment against the use of antibiotics, growth hormones and the like in livestock and fish to be consumed by humans.

There has been some success in the use of vaccines, notably against diseases such as vibriosis and enteric red mouth. But there are still diseases for which vaccines are not effective or are of inadequate efficacy.

It is known in medicine that the efficacy of certain vaccines can be improved by the administration of compounds in addition to the vaccines.

It is known that certain glucans can be useful in curing human cancer by an apparent immunomodulating effect. Glucans are the anhydrides of glucose derivatives, for example cellulose, starch, dextrin and glycogen.

Relevant patents relating to glucans known to applicant include U.S. Pat. Nos. 4,098,661 issued Jul. 4, 1978, British Patent 1,061,043 dated Oct. 23, 1963 and Canadian Patent 968,286 issued May 27, 1975.

SUMMARY OF THE INVENTION

It has now been observed that certain glucans exhibit appreciable, advantageous effect in the use of vaccines for treating fish diseases. Of particular interest are $\beta$-1,3 glucans and particularly the compounds schizophyllan (SPG) and scleroglucan. These water soluble $\beta$-1,3 glucans are reported to have triple helical structures. Schizophyllan is prepared by the precipitation in a culture filtrate of the fungi Schizophyllum commune, using acetone, ethanol or other water miscible solvent as a precipitant. Sceleroglucan is obtained in a similar manner from a culture filtrate of a selected species of Sclerotium. The above compounds are represented by the following structural formulae:

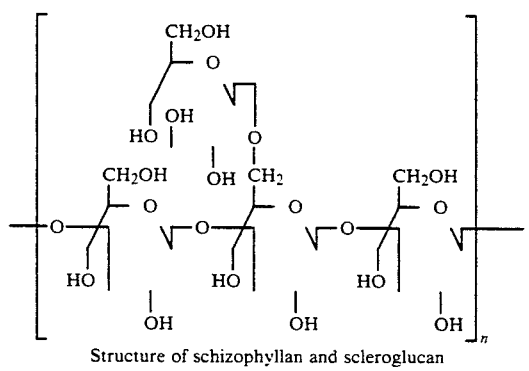

Structure of schizophyllan and scleroglucan

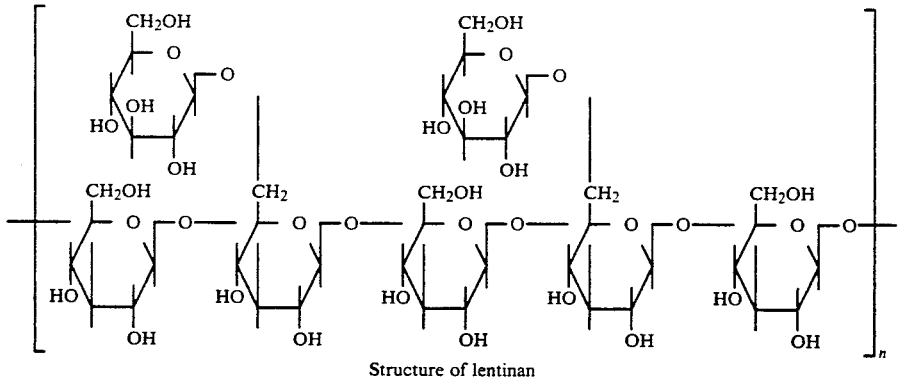

Structure of lentinan

The present invention is thus directed to the immuno stimulating and vaccine enhancing effects of $\beta$-1,3 glucans and is based on the surprising observation that these compounds are effective in the treatment of fish and in vaccine prophylaxis in fish.

Accordingly, in a first aspect, the present invention is a process to stimulate the efficacy of a fish vaccine that comprises administering to a fish treated with the vaccine a $\beta$-1,3-glucan having a $\beta$-1,3-linked main chain with $\beta$-1,6-linked single glucose side chains.

In a further aspect the invention is a process to stimulate the immune system of fish that comprises administering to the fish a $\beta$-1,3-glucan as defined above.

In yet a further aspect the invention is a composition able to enhance the efficacy of a fish vaccine and comprising a β-1,3-glucan having β-1,3-linked main chain with β-1,6-linked single glucose side chains in combination with a carrier acceptable to fish.

The carrier will typically be saline for injectable compositions and food for compositions to be administered by mouth. With advantage alpha-cellulose may be mixed with the glucan prior to mixing with food.

In a particularly preferred embodiment the invention provides a composition to enhance the efficacy of a fish vaccine comprising an antigen source and a β-1,3-glucan having a β-1,3-linked main chain with β-1,6-linked single glucose side chains. Preferably the antigen source is a vaccine.

BRIEF DESCRIPTION OF THE DRAWING

FIG. 1 relates cumulative mortality to time in certain comparative experiments described in the Experimental Work below.

EXPERIMENTAL WORK

Experimental procedures were developed to determine the ability of certain β-1,3-glucans to enhance the performance of formalin killed bacterin and stimulate the non-specific immune system of salmonid fishes such that they can show increased survival during a virulent challenge. The model system chosen for the challenge was *Aeromonas salmonicida* the etiological agent of furunculosis, because of the reported involvement of cell mediated immunity in this disease. Cell mediated immunity plays a major role in immune protection against bacterial kidney disease (BKD), another disease that plagues aquaculture fish, but the course of infection is long, necessitating the use of a furunculosis model system.

Two systems of challenge were used. First immersion, secondly cohabitation. The mortality figures were then adjusted by calculating relative potency so that the comparisons could be made between the two challenge groups. Relative potency showed good reproducibility between tanks and lentinan and schizophyllan enhanced vaccines were both found to have similar level of potency within and between tanks. The relative potency was determined according to Table 1. Relative potency is defined as percentage mortality in the control divided by the percentage mortality in the vaccinates.

The results are set out in Table 1.

TABLE 1

Enhancement of efficacy of injection-delivered vaccine by the β-1,3 Glucans, Lentinan and Schizophyllan (SPG).

| Challenge Method | Treatment | % Mort. | *Relative Potency |
|---|---|---|---|
| Immersion | Lentinan + Ag | 60% | 1.6 |
| | SPG + Ag | 64% | 1.5 |
| | Antigen only | 96% | 1.0 |
| Cohabitation | Lentinan + Ag | 52% | 1.6 |
| | SPG + Ag | 52% | 1.6 |
| | Antigen only | 84% | 1.0 |

*Relative Potency is defined as follows:
$$RP = \frac{\% \text{ Mortality (Control)}}{\% \text{ Mortality (Vaccinates)}}$$

Because of the similarity in structure function further experimental work was conducted with one compound, schizophyllan. This compound is less costly to produce than lentinan. It can be produced by batch fermentation but lentinan must be extracted from the fruiting body of the mushroom *Lentinus edodes*, which is a popular food in Japan and elsewhere, making the compound lentinan expensive.

In the next phase of experiments SPG was obtained in three different forms. First a purified and extensively depolymerized form (SPG-P). Secondly a crude extract with only slight depolymerization (SPG-C) and, thirdly, a crude preparation of native SPG in culture broth containing pulverized mycelia (SPG-M).

These forms of SPG were administered to fish by intraperitoneal (i.p.) injection in an admixture containing *A. salmonicida* bacterin and one each of the three different forms of SPG. Fish were then challenged by immersion in virulent *A. salmonicida* and the resulting mortalities were monitored. The results are in Table 2.

TABLE 2

Differences in Efficacy of various molecular weight forms of SPG.

| Treatment received | % mortality replicate 1 | % mortality replicate 2 | pooled % mort. |
|---|---|---|---|
| SPG-m1 + Ag | 6.7% | 26.7% | 16.7% |
| SPG-c2 + Ag | 60.0% | 3.3% | 31.7% |
| SPG-p3 + Ag | 56.7% | 66.7% | 61.7% |
| Ag only | 33.3% | 20.0% | 26.7% |
| saline | 76.7% | 66.7% | 71.7% |

1 SPG-m designates the crudest form of SPG. This is a preparation of colloidaly pulverized mycelia containing the highest molecular weight of SPG.
2 SPG-c is a crude form of SPG that has been somewhat purified and somewhat depolymerized.
3 SPG-p is the purified and depolymerized form of SPG.

It is seen from the above that the crudest form of SPG (SPG-M) was the most effective. With a decrease in molecular weight there was a decline in the level of enhancement to the vaccine.

A further series of experiments was conducted to assess the efficacy of SPG as a non-specific chemoprophylactant. It was found that when injected i.p. at the rate of 20 mg/kg 20 days prior to challenge, fish were protected for at least 40 days after injection to a similar extent to fish that received an i.p. delivered vaccine consisting of antigen alone. These results are summarized in FIG. 1, which graphically relates cumulative percentage mortality to time. The curve is a mortality curve showing saline-injected fish compared with fish injected with SPG alone and with antigen alone. Fish injected with SPG alone show a similar level of protection to those vaccinated with antigen only. This protection seems to last about 20 days after challenge. The fish were injected with the SPG and the antigen 20 days before day zero of the curve of FIG. 1.

Thus the results show that β-1,3-glucans are effective both as a means of stimulating the immune system of fish and as a means of improving the efficacy of vaccines.

The results show effect against *A. salmonicida*, the causative agent in furunculosis for which published vaccination attempts have yielded poor results. But the same effect could, it is believed, be achieved against bacterial kidney disease (BKD) caused by the organism Renibacterium salmoninarum which is also a pathogen of salmonid fish.

The above experimental results are directed to fish belonging to the family salmonidae. However, the experimental results are equally applicable to other species, for example ornamental fishes, pet, hobby fishes, carp, sea bream and the like. In particular there is nothing that would lead the skilled worker to believe that the compositions are not effective for all fish but the invention is of particular interest in the treatment of aquaculture fish. There is a substantial homogeneity in the immune systems of all fish species.

We claim:

1. A method to enhance the efficacy of a fish vaccine that comprises administering to a fish treated with the vaccine a β-1,3-glucan having a β-1,3-linked main chain with β-1,6-linked single glucose side chains.

2. A method as claimed in claim 1 in which the vaccine is one effective against *Aeromonas salmonicida*.

3. A method as claimed in claim 1 in which the fish is a species belonging to the family salmonidae.

4. A method as claimed in claim 1 in which the glucan is scleroglucan.

5. A method as claimed in claim 1 in which the glucan is schizophyllan (SPG).

6. A method as claimed in claim 5 in which the schizophyllan is used in the form of an unpurified extract.

7. A method as claimed in claim 6 in which the extract is native schizophyllan in a culture broth containing pulverized mycelia.

8. A method as claimed in claim 1 in which the β-1,3-glucan is administered orally.

9. A method as claimed in claim 1 in which the dose of β-1,3-glucan is in the range 15 to 20 mg per kilogram body weight.

* * * * *